(12) United States Patent
Bahr

(10) Patent No.: US 9,161,430 B1
(45) Date of Patent: Oct. 13, 2015

(54) HELICAL RESONATOR ION ACCELERATOR AND NEUTRON BEAM DEVICE

(71) Applicant: Dennis E. Bahr, Middleton, WI (US)

(72) Inventor: Dennis E. Bahr, Middleton, WI (US)

(73) Assignee: HELIONX LLC, Middleton, WI (US)

( * ) Notice: Subject to any disclaimer, the term of this patent is extended or adjusted under 35 U.S.C. 154(b) by 69 days.

(21) Appl. No.: 14/032,803

(22) Filed: Sep. 20, 2013

Related U.S. Application Data

(60) Provisional application No. 61/703,696, filed on Sep. 20, 2012.

(51) Int. Cl.
*H05H 3/06* (2006.01)
*G01T 3/00* (2006.01)
*G01N 23/05* (2006.01)

(52) U.S. Cl.
CPC .............. *H05H 3/06* (2013.01); *G01N 23/05* (2013.01); *G01T 3/00* (2013.01)

(58) Field of Classification Search
CPC ............. H05H 3/06; G01N 23/05; G01T 3/00
See application file for complete search history.

(56) References Cited

U.S. PATENT DOCUMENTS

| | | | | |
|---|---|---|---|---|
| 6,777,699 B1* | 8/2004 | Miley et al. | ................. | 250/492.3 |
| 6,907,097 B2 | 6/2005 | Leung | | |
| 2011/0085632 A1* | 4/2011 | Klein et al. | .................... | 376/129 |
| 2012/0328066 A1* | 12/2012 | Burke et al. | ................... | 376/111 |

OTHER PUBLICATIONS

G.J. Caporaso, R.J. Briggs, B.R. Poole, S.D. Nelson, "Dispersion Analysis of the Pulseline Accelerator," Proceedings of 2005 Particle Accelerator Conference, Knoxville, Tennessee.
S.D. Nelson, G. Caporaso, A. Friedman, B.R. Poole, R. Briggs, W. Waldron, "Electromagnetic Simulations of Helical-based Ion Acceleration Structures," 2005 Particle Accelerator Conference, Knoxville, Tennessee, May 9, 2005.
W.L. Waldron, L.L. Reginato, E. Henestroza, A. Friedman, R.J. Briggs, "Studies of the Pulse Line Ion Accelerator," Proceedings of PAC07, Albuquerque, New Mexico.
A. Friedman, R.J. Briggs, D.P. Grote, E. Henestroza, and W.L. Waldron, "Modeling the Pulse Line Ion Accelerator (PLIA): an algorithm for quasi-static field solution.".
Richard J. Briggs, "Pulse line ion accelerator concept," Physical Review Special Topics—Accelerators and Beams, Jun. 21, 2006.

* cited by examiner

*Primary Examiner* — David Porta
*Assistant Examiner* — Mindy Vu
(74) *Attorney, Agent, or Firm* — Stiennon & Stiennon

(57) ABSTRACT

A Helical Resonator Ion Accelerator in which ions are injected into a hollow dielectric pipe forming a vacuum chamber along which the ions are accelerated. The pipe is wrapped with a coil and positioned inside a metal pipe. The dielectric pipe, the coil and the metal pipe are arranged coaxially on an axis along which ions are accelerated. The metal pipe is positioned within a high intensity 0.5-3.0 Tesla solenoid. A pulse generator is coupled to the coil to generate a voltage wave pulse. The pulse travels down the axis of the accelerator on the helix formed by the coil. An ion source injects deuteron ions along the axis of the vacuum chamber. A traveling voltage wave is accelerated by tapering the characteristic velocity of the accelerator in the direction of wave propagation by tapering the coil and the outer metal pipe together in a constant ratio.

7 Claims, 9 Drawing Sheets

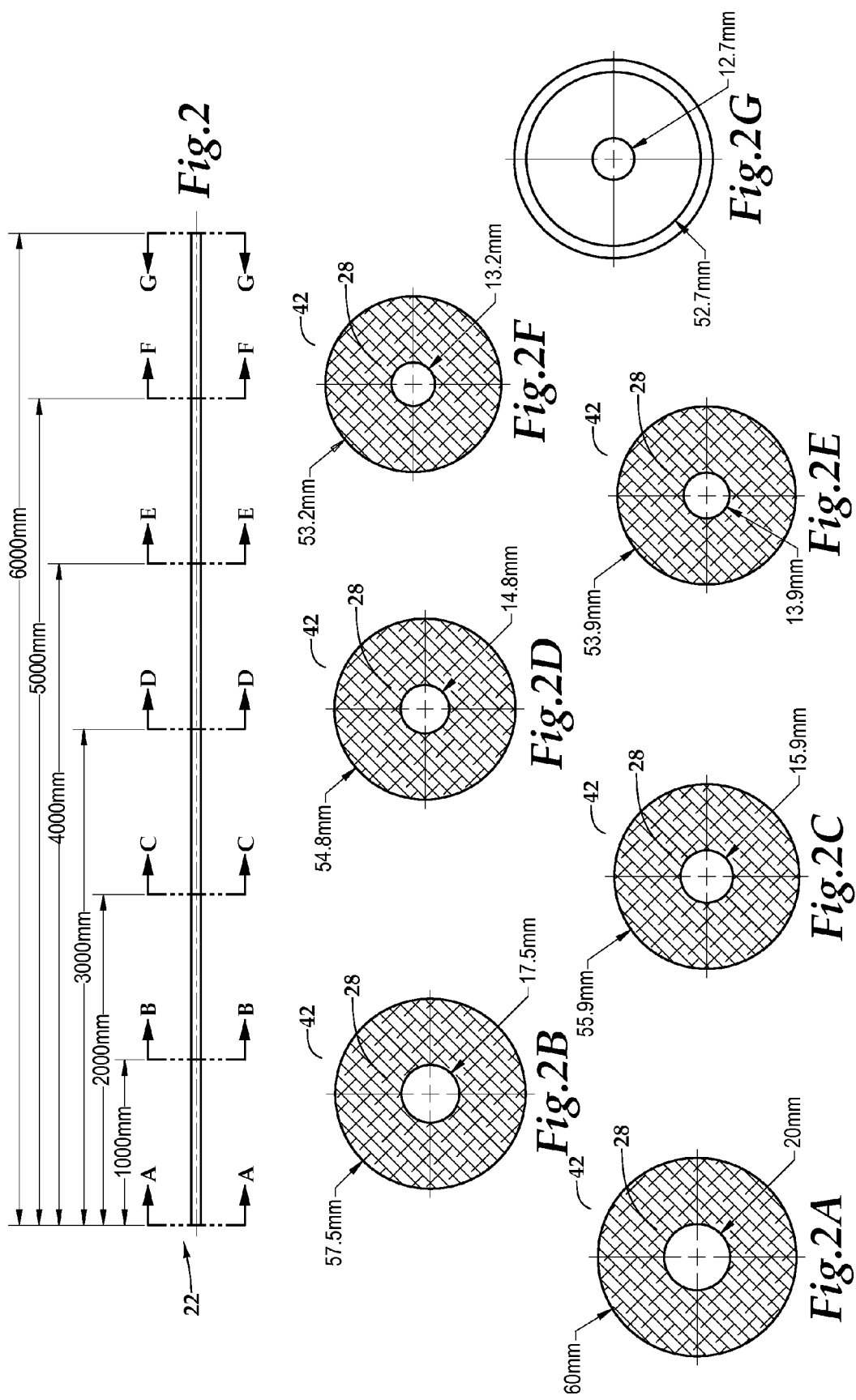

HELICAL RESONATOR ION ACCELERATOR AND NEUTRON BEAM DEVICE

CROSS REFERENCES TO RELATED APPLICATIONS

This application claims priority on provisional application U.S. App. No. 61/703,696 filed on Sep. 20, 2012, to Dennis E. Bahr, which is incorporated herein by reference.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The present invention relates to ion accelerators in general and to helical ion accelerators in particular. Accelerators of ions have many practical uses in addition to basic research which vary from ion implantation, such as used to form semiconductors or coatings, to neutron radiography used to detect explosives and nuclear materials in luggage and shipping containers. The development of the helical ion accelerator, also called a pulse line ion accelerator, was motivated by the desire for a less expensive way to accelerate intense short pulse heavy ion beams to regimes of interest for studies of high energy density physics and warm dense matter. In helical ion accelerators a pulse power driver applied at one end of a helical pulse line creates a traveling wave pulse that accelerates and axially confines a heavy ion beam pulse. Richard Briggs described acceleration scenarios with constant parameter helical lines which result in output energies of a single stage much larger than the several hundred kilovolt peak voltages on the line. The concept can be described as an "air core" coax line where a pulse is injected into a central helical core so that an accelerating voltage pulse moves along with the ions to get voltage multiplication.

SUMMARY OF THE INVENTION

The Helical Resonator Ion Accelerator of this invention comprises an ion source preferably of deuteron ions arranged to inject ions into a hollow dielectric pipe forming a vacuum chamber. The hollow pipe defines an axis along which particles are accelerated. The hollow pipe is wrapped with a coil, defining a proximal end and a distal end, and the coil is placed inside a metal outer pipe. The dielectric pipe, the coil and the metal pipe are arranged coaxially to an axis of the accelerator substantially along which particles are accelerated. A material with a high electrical breakdown voltage such as dielectric oil or sulfur hexafluoride ($SF_6$) at one to several atmospheres of pressure fills a void formed between the coil and the outer metal pipe. The outer metal pipe is positioned within the high intensity (e.g. 0.5-3.0 Tesla) solenoid magnetic field such as produced by a superconducting solenoid, to provide continuous axial focusing of the deuteron beam. A pulse generator is coupled to the proximal end of the coil, to generate a voltage wave form pulse which is coupled to the coil. The pulse then travels down the axis of the accelerator on the coil (not traveling directly on the wire but axially on the helix formed by the coil). The voltage pulse has a voltage on the order of 100-300 kV. The coupling of the pulse generator may use a resistive column to match impedance of the coil, or use an inductive couple of one or a few turns so that a high current pulse in the inductive coil induces a high-voltage pulse in the coil. A third and perhaps most economical approach is to charge the outer pipe relative to the coil to a voltage on the order of 100-300 kV, and create the drive pulse by shorting the outer metal pipe to the coil at the proximal end of the coil.

In order to prevent the injected voltage waveform reflecting from the distal end of the coil, the coil is grounded to a matching resistive network/column. In the case where the high-voltage pulse is injected using impedance matching resistance network, the output of the coil through a further matching resistive network/column can be conducted to a directional coupler allowing use of a waveform generator to output a waveform which adds to the output of the coil which can be recirculated to the proximal end of the coil and reinjected into the coil through the resistive network/column.

Ion injection is, for example, a Helicon type plasma injector and ion source which injects deuteron ions along the axis of the vacuum chamber formed by the hollow dielectric pipe.

In order to achieve maximum acceleration of any ion it is necessary that the velocity of the electric field accelerate as it moves along the axis of the accelerator, otherwise the ions will have a constant velocity. Traveling wave velocity can be accelerated by tapering the characteristic velocity of the accelerator in the direction of wave propagation (i.e., increasing the velocity per unit length). This may be accomplished, for example, by varying the geometry of the accelerator by tapering the coil and the outer metal pipe or decreasing the number of turns of the coil per meter along the axis of acceleration. In one preferred embodiment the diameter of the metal pipe and diameter of the coil are tapered together in a constant ratio and the number of turns of the coil per meter is held constant.

The Helical Resonator Ion Accelerator can have a pulse repetition rate of 10-100 pulses/second, a pulse duration of about $5 \times 10^{-9}$ seconds, and an average power of 1-10 kilowatts. Deuteron ions are injected into the proximal end of the accelerator with injection velocity of about 25 key or 1.55 meters/microsecond, and the final velocity achieved by the accelerator as calculated is about 5.4 Mev or 22 meters/microsecond for an accelerator length of about 6 meters. Only about 2 Mev are required to reach the peak cross-section of the D+D→He+n (2.45 Mev) as shown in FIG. 5 of U.S. Pat. No. 6,907,097.

If the ions are deuteron ions they are directed at a target containing deuteron atoms, typically absorbed as $D_2$ in a thin layer of Titanium or palladium on a thermally conductive substrate such as copper or silver.

It is an object of the present invention to produce a lower cost compact accelerator of deuterons.

It is another object of the present invention to provide the equations designing a tapered helical pulse line ion accelerator.

Is a further object of the present invention to provide well focused short deuteron pulses which can be used to interrogate goods within packages, suitcases, or shipping containers.

Further objects, features and advantages of the invention will be apparent from the following detailed description when taken in conjunction with the accompanying drawings.

BRIEF DESCRIPTION OF THE DRAWINGS

FIG. 2-2G are a schematic front elevational view combined with cross-sectional views A-A to F-F and end wall view G-G.

DESCRIPTION OF THE PREFERRED EMBODIMENTS

Figure 1:
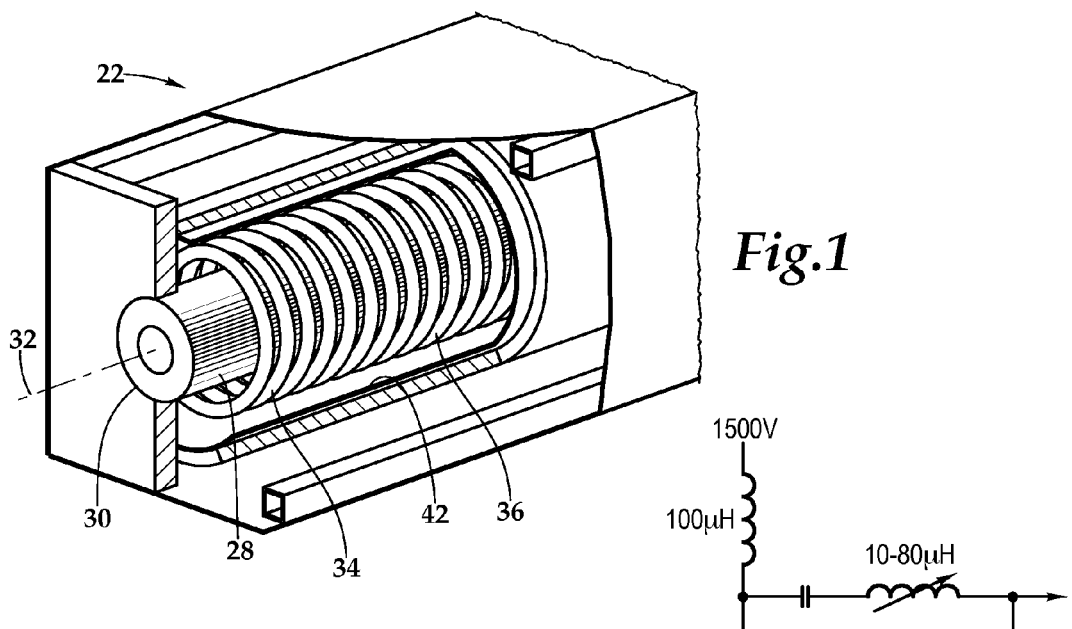
FIG. 1 is an front elevational isometric view of a pulse line ion accelerator.
Figure 3:
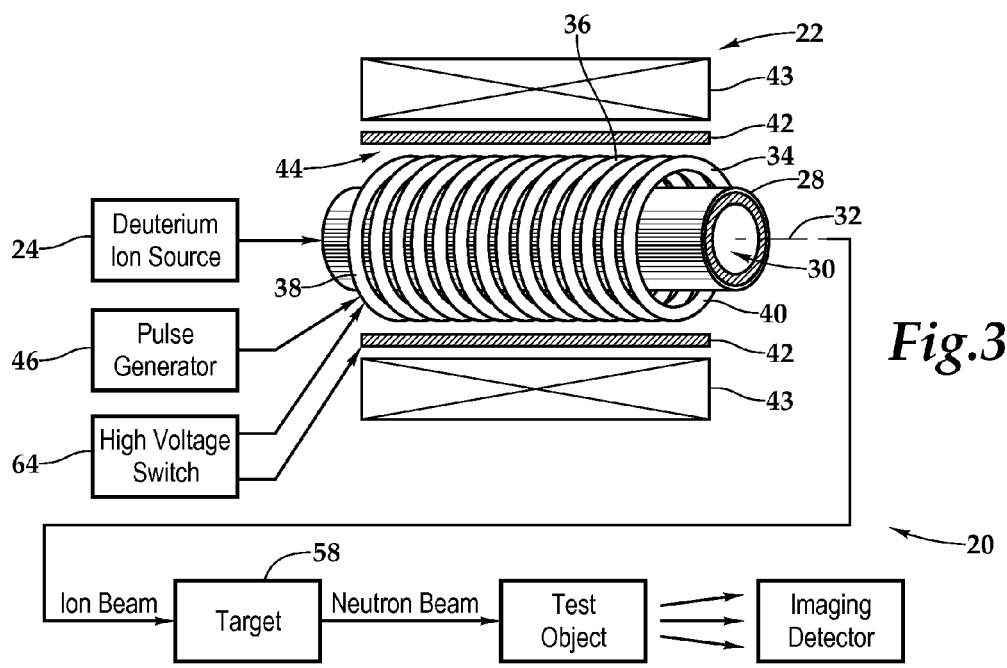
FIG. 3 is a schematic illustration of the neutron inspection device of this invention.

Referring more particularly to FIGS. 1-3, wherein like numbers refer to similar parts, a helical resonator ion accelerator 22 is shown in FIG. 1 and schematically in FIGS. 2-2G, and as part of a neutron inspection device 20 in FIG. 3. The Helical Resonator Ion Accelerator 22 has a deuteron ion source 24 arranged to inject deuteron ions 60 with a velocity of injection of about 25 kV or 1.5 meters/microsecond along a central axis of a helical ion accelerator into a hollow dielectric pipe 28 forming a vacuum chamber 30. The dielectric pipe 28 defines an axis 32 along which particles are accelerated. The dielectric pipe 28 is wrapped with wire 34 to form a coil 36, defining a proximal end 38 and a distal end 40, and the coil is placed inside a metal outer pipe 42. As shown in FIG. 3 a dielectric pipe 28, the coil 36 and the metal pipe 42 are arranged coaxially to the axis 32 of the accelerator substantially along which particles are accelerated. The coil 36 is wound in accord to the minimum wire spacing as explained below.

A highly efficient helical particle accelerator is described that overcomes a number of problems and limitations of previous designs. By mathematically representing the device as a transmission line, existing equations can be used to calculate parameters to optimize the function and efficiency.

Space wound helical coils such as coil 36 are wound such that there is space between adjacent windings. The effective resistance increases due to the proximity effect when two or more wires are wound into a coil The effective resistance is a combination of three terms, the proximity effect, the skin effect, and the bulk resistance. Wire spacing and wire radius on coils with two or more turns, as the number of turns increases, the wire spacing reaches a spacing asymptote of approximately 1.8. The space between wires for a long solenoid for the minimum resistance can be calculated as follows:

Wire spacing=$2c-2a=2\times1.8Ca-2\times a=1.6\times a$

Helical accelerators can be designed using a lossy resistive terminator mode, a resonance mode, or a traveling wave mode. In any of these modes the particle must be injected during the correct phase of the exciting voltage to provide the optimum acceleration. The current method using a helical accelerator is usually accomplished by generating a saw tooth wave form, launching it on one end of the accelerator, and capturing it on the distal end with a resistive terminator to prevent reflections. This process is very inefficient and generates a significant amount of heat in the resistive terminator.

This invention describes two methods for building helical accelerators. In the resonance mode the helix is used as an open resonator with no external shield or as an enclosed resonator that resembles a resonant coaxial cable. In either case the helix can be resonated in either quarter wave ($\pi/4$) or half wave ($\pi/2$) mode. The preferred method is the $\pi/2$ mode since the peak voltages are found in the center of the helix.

Figure 5:
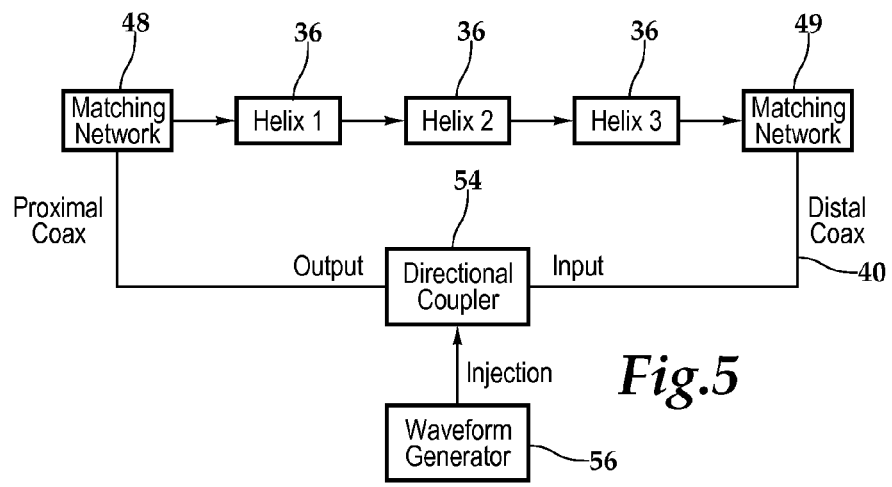
FIG. 5 is a schematic diagram of a traveling wave mode accelerator of this invention.
Figure 6:
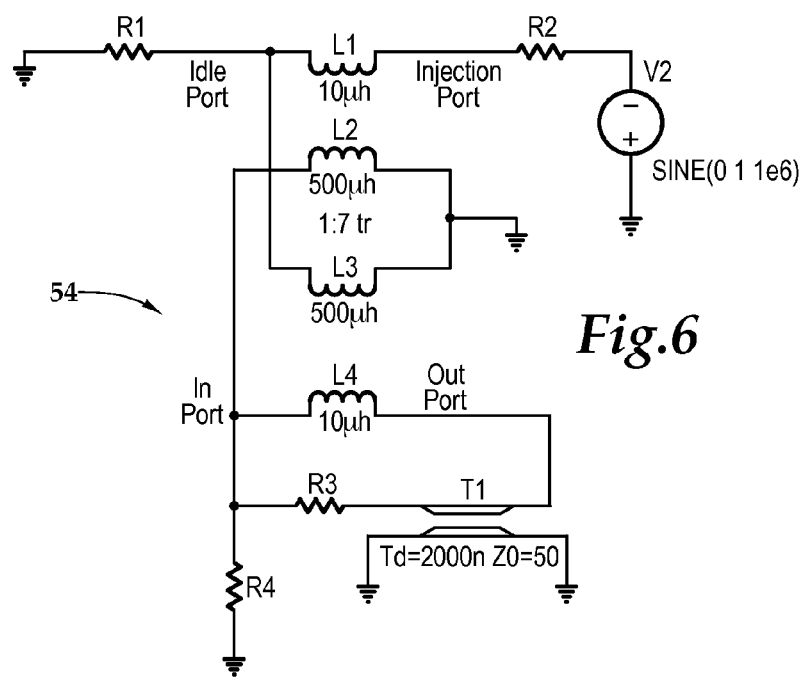
FIG. 6 is an electrical schematic of the directional coupler of the traveling wave mode accelerator FIG. 5.

In the traveling wave mode, which is shown in FIG. 5, a waveform is launched toward the proximal end of the coil and travels along the helix carrying any ion particles along with the wave. At the distal end of the accelerator the wave is captured and returned to the proximal end. Before the wave is again injected in the proximal end the system adds enough energy to compensate for system losses including beam loading.

The process begins by injecting a sine wave signal into the directional coupler shown in FIG. 5. The coupler will pass the signal to the proximal coax but not to the distal coax. Using a Spice model the directionality of the coupler was found to be +38 dB in the direction of the proximal coax. The coax can be parallel coupled or link coupled to a helix coil and a matching circuit may be required since the characteristic impedance of the helix is between 1000 and 2000 Ohms.

At the distal end the signal is removed from the coil and transferred to a second coaxial cable using similar matching techniques as is done on the proximal end. The wave entering the coupler and the injected wave must be in phase with each other so that enhancement will take place. The helical coil has a maximum frequency in the mid 100 kHz range. If the helix is to be resonated, MatLab models have shown that the half wave resonance is approximately 4 MHz in each of the two resonators.

The modeled coil was 0.56 meters long with a circumference of 0.28 meters and a pitch of 0.0025 meters. The wire length is thus 57.2 meters. The wire is insulated 16 AWG magnet wire. The coil contains 200 turns of wire spaced to minimize the resistive effects from skin effect and proximity effect. Knowing the group velocity and the physical characteristics of the coil, the phase velocity can be calculated.

$v_g$=40 m/μs
$C_t$=0.508 m $$C_t = \frac{0.508}{4.0} = 0.127 \text{ μs}$$

$W_l$=57.2 m $$v_p = \frac{57.2}{0.127} = 450 \frac{m}{\mu s}$$

The phase velocity $v_g$ appears to be exceeding the velocity of light. This occurs because the axial wave is not traveling directly on the wire, but instead is actually skipping wires while traveling axially on the helix.

The ion particles can be injected at a point on the waveform where the electric field in front of the particle is "pulling" on the particle. As the ion enters the helix the electric field behind the ion particle will "push" on the particle accelerating it to the distal end of the helix. A second helix, with a faster wave speed, could follow the first helix and add yet more acceleration. This could continue for any number of helices to provide the required ion particle velocity.

A pulse could be used in lieu of a sine wave to accelerate the ion beam using the helical structure. The advantage of a pulse is that the electric field will be significantly larger due to the rising edge of the pulse. One method of generating microsecond pulses with nanosecond rise and fall times is to use a Blumlein generator. These devices can be built using discrete components or coaxial transmission lines. If stacked Blumleins are used the characteristic output impedance can become significant (200 to 1000 Ohms). However, the increase in output impedance can be used to match the Blumlein to the helical ion accelerator which also has high characteristic impedance.

Another component of the invention is the calculation of the tapering of the helix to provide constant acceleration on the ion beam. Assuming that one applies a constant force, the velocity of the particle will increase linearly to a first order approximation.

L=>f(n²)
C=>f(n)
v=1/√L×c $$v => \frac{1}{\sqrt{f_1(n^2) \times f_2(n)}}$$

$$v => 1 \Big/ f_3\!\left(n^{\frac{3}{2}}\right)$$

v=k₁×x $$n = k_2 \times x^{\frac{-2}{3}}$$

L=inductance/unit L
C=capacitance/unit L
n=number of turns/unit L
v=particle velocity
x=fractional position along accelerator
$k_1$ and $k_2$=constants
Therefore, n/ul varies as $x^{-2/3}$.

As shown in FIG. 5 the output from the waveform generator is steered towards the output and the proximal coax. The matching network converts the 50-75 Ohm coax characteristic impedance to the 1000-2000 Ohm helix impedance. As the wave travels from left to right, through the helices, it accelerates any ions in the center of these helices. The ion beam continues traveling to the right while the wave is captured, matched, and returned to the directional coupler.

And, as shown in FIG. 5, the directional coupler connects the distal end of the helix to the proximal end while adding additional energy at the injection port to compensate for system and ion coupling losses.

As shown in FIG. 1, a material with a high electrical breakdown such as dielectric oil or sulfur hexafluoride ($SF_6$) at one to several atmospheres of pressure fills a void 44 formed between the coil 36 and the outer metal pipe 42. The outer metal pipe 42 is positioned within a high intensity (e.g. 0.5-3.0 Tesla) solenoid magnetic field such as produced by a superconducting solenoid 43, to provide continuous axial focusing of the accelerated deuteron beam. A pulse generator 46 such as a Blumlein transmission line or a pulse forming network (PFN) is coupled to the proximal end 38 of the coil 36, to generate a voltage waveform pulse which is thus coupled to the coil 36. The voltage pulse then travels down the axis 32 of the accelerator 22. The axial wave does not traveling directly on the wire but skips wires while traveling axially on the helix formed by the coil 36. The voltage pulse has a voltage on the order of 100-300 kV. The coupling of the pulse generator may use a resistive column to match impedance, or use an inductive couple of one or a few turns so that a high current pulse in the inductive coil induces a high-voltage pulse in the coil 36. A third and perhaps most economical approach is to charge the outer metal pipe 42 relative to the coil to a voltage on the order of 100-300 kV, and create the drive pulse by shorting the outer metal pipe to the coil 36 with a high voltage switch 64 at the proximal end 38.

Figure 4:
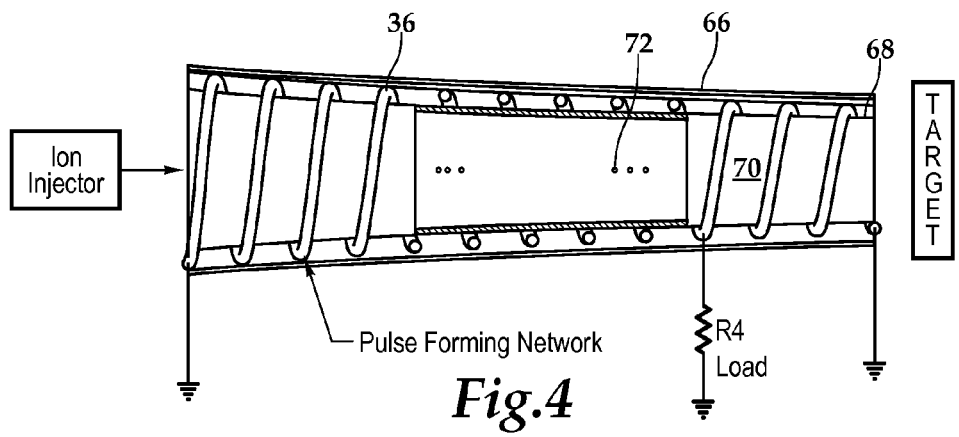
FIG. 4 is partly cut-away front elevational view of a preferred embodiment where the diameter of the metal pipe and diameter of the insulator and the coil are conically tapered together in a constant ratio and the number of turns of the coil per meter is held constant.

In order to prevent the injected voltage waveform from reflecting from the distal end 40 of the coil, the coil is grounded to a matching resistive network/column. In the case where the high-voltage pulse is injected using impedance matching using a resistance network/column, the output of the coil is through a further matching resistive network/column and can be conducted to a directional coupler 54 to allow use of a waveform generator 56 to output a waveform which adds to the output of the coil 36 which can be recirculated to the proximal end 38 of the coil 36 and reinjected into the coil 48 as shown in FIG. 4.

Ion injection is, for example, a Helicon type plasma injector and ion source which injects deuteron ions along the axis 32 of the vacuum chamber 30 formed by the hollow dielectric pipe 28.

The design of the accelerator 22 is based on equations below where it is shown how the accelerator geometry or winding pitch can be selected to achieve a desired acceleration of the injected electric pulse and therefore the injected ions. A design based on using these equations to model systems is shown in FIGS. 2-2G.

In order to achieve maximum acceleration of the deuteron ions it is necessary that the velocity of the electric field accelerate as it moves along the axis of the accelerator, otherwise the ions will outrun the traveling wave having a constant velocity in the accelerator tube 28. The traveling wave velocity can be accelerated by tapering the impedance of the accelerator in the direction of wave propagation (i.e., reducing the impedance per unit length). This may be accomplished for example by varying the geometry of the accelerator by tapering the coil and the outer metal pipe or decreasing the number of turns of the coil per meter along the axis of acceleration. See below equations of design and their derivation. In one preferred embodiment, shown in FIG. 4, the diameter of the metal pipe 66 and the diameter of the coil 36, the dielectric conical pipe 68 defining an outer conical surface 70 are tapered together in a constant ratio and the number of turns of the coil per meter is held constant. Ions 72 are shown in the vacuum with in the dielectric conical pipe 68.

The Helical Resonator Ion Accelerator 22 can have a pulse repetition rate of 10-100 pulses/second, a pulse duration of about $5 \times 10^{-9}$ seconds, and an average power of 1-10 kilowatts. Deuteron ions can be injected into the proximal end 38 of the accelerator 22 with an injection velocity of from about 18 keV, 1.3 m/μsec, to about 25 keV or 1.5 meters/microsecond, and the final velocity achieved by the accelerator as calculated is about 5.4 MeV or 20.2 meters/microsecond for an accelerator length of about 6 meters.

Figure 11:
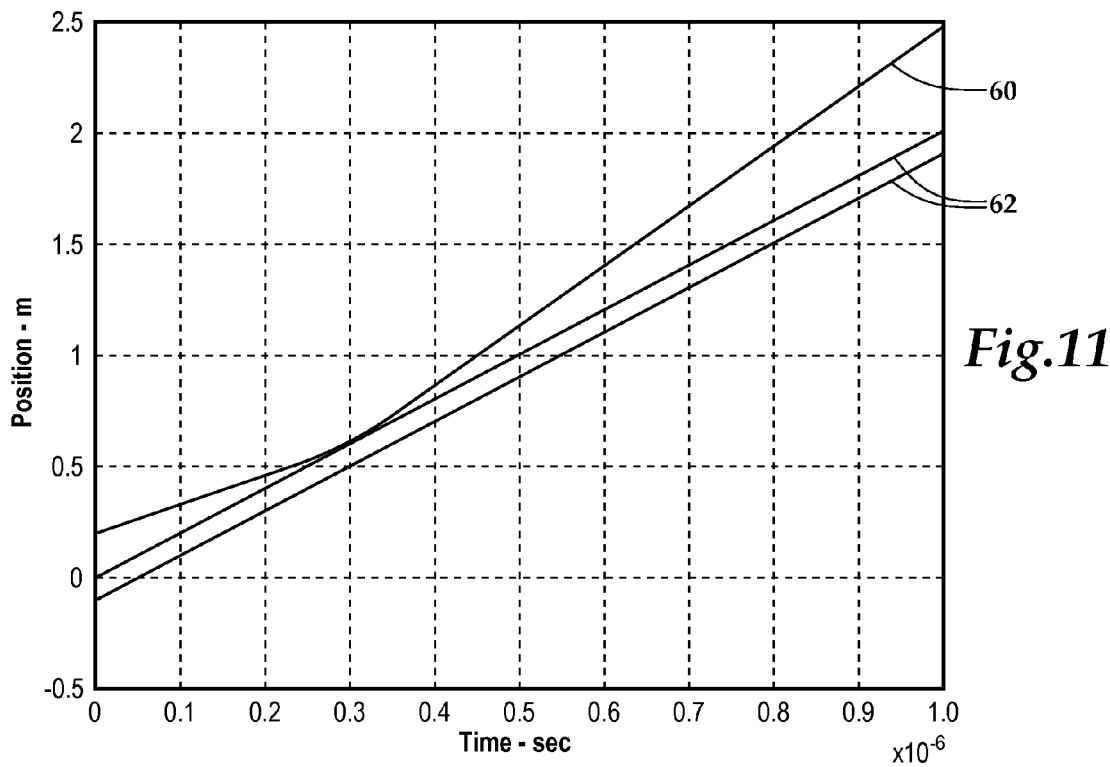
FIG. 11 is a graphical view of the velocity gain with the input velocity of FIG. 10.
Figure 12:
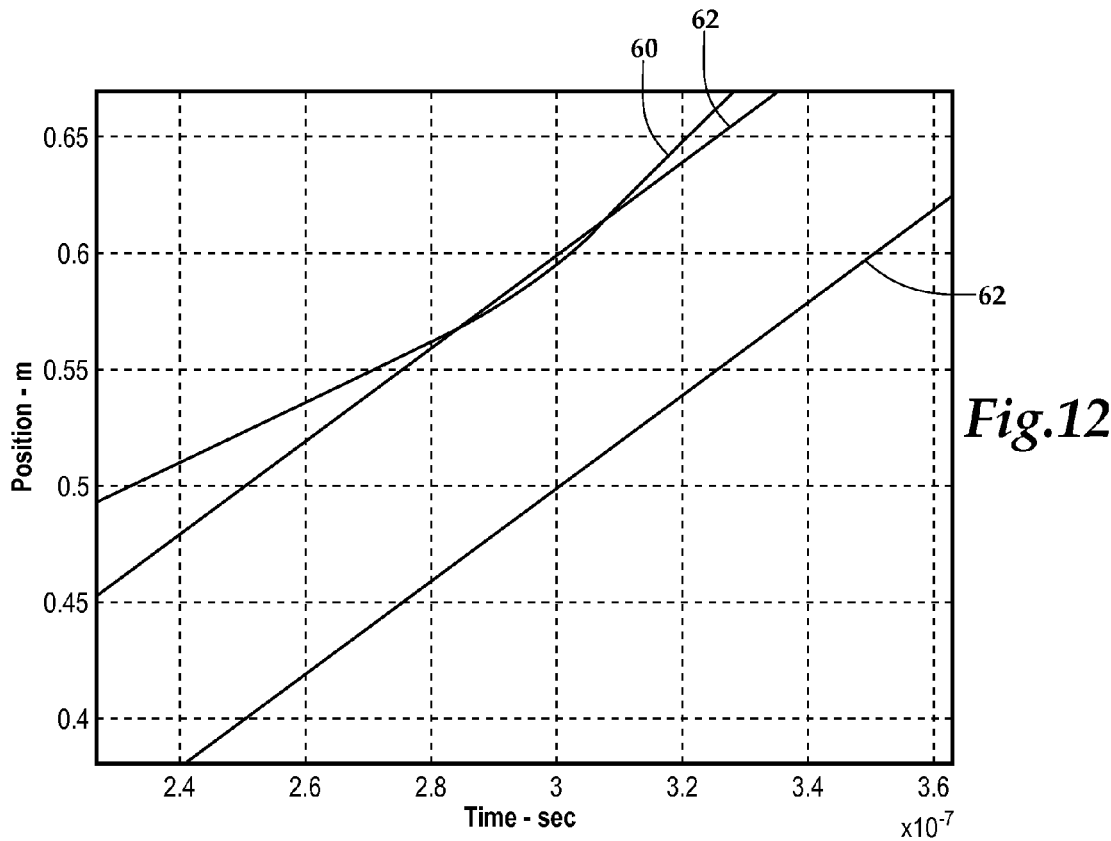
FIG. 12 is a graphical view of an enlarged portion of the graph of FIG. 11.
Figure 13:
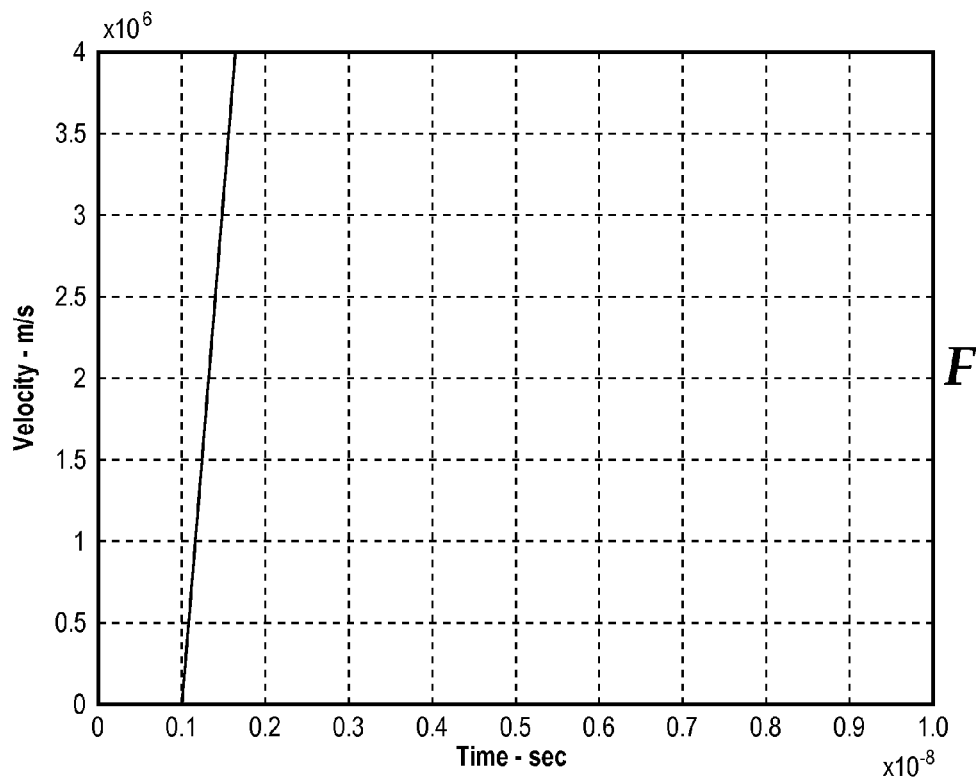
FIG. 13 is a graphical view of an input velocity of 0 m/s.
Figure 14:
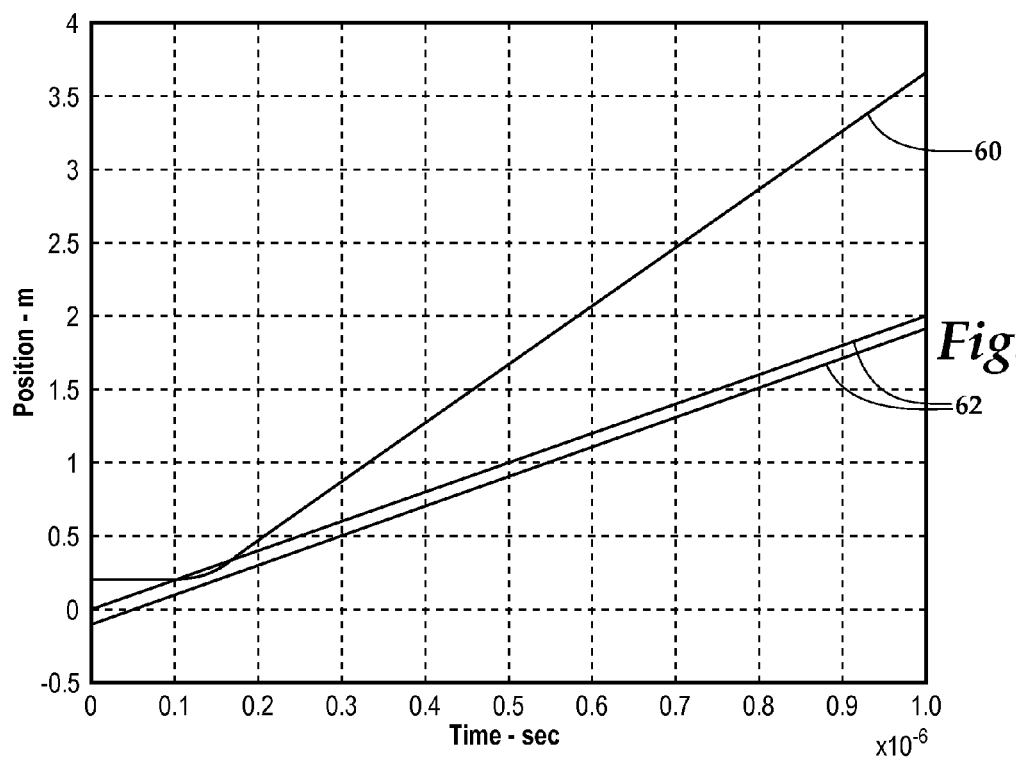
FIG. 14 is a graphical view of the velocity gain with the input velocity of FIG. 13.
Figure 15:
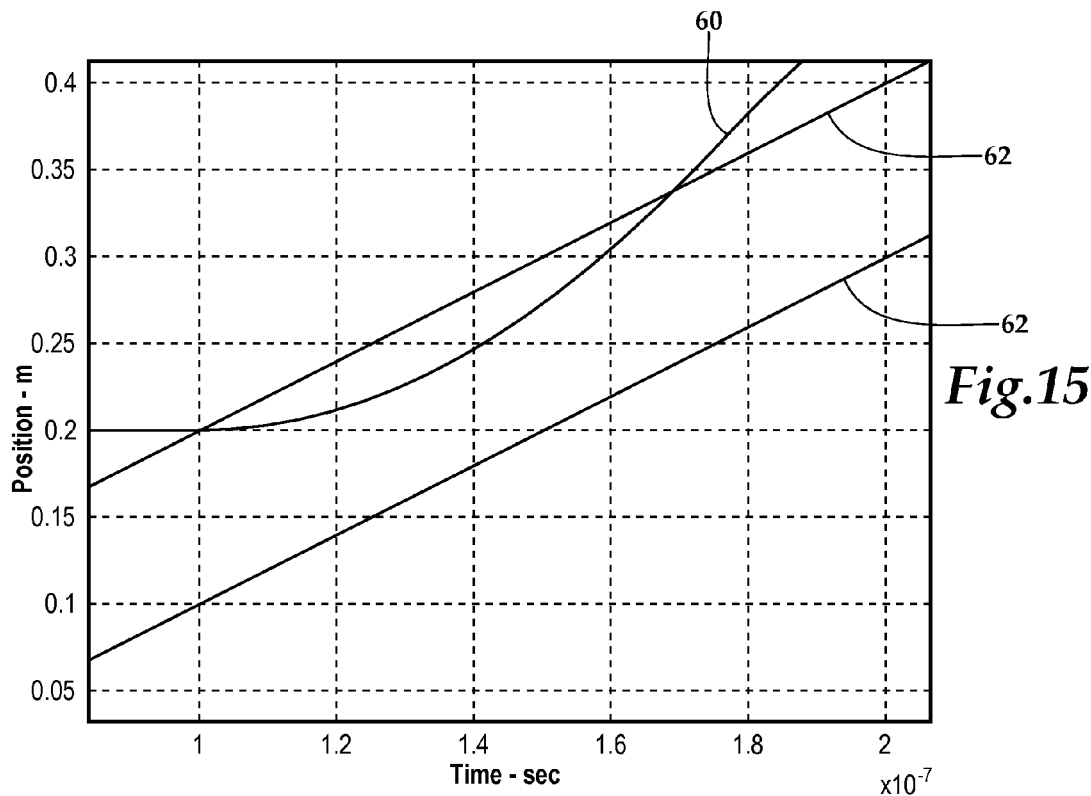
FIG. 15 is a graphical view of an enlarged portion of graph of FIG. 14.
Figure 16:
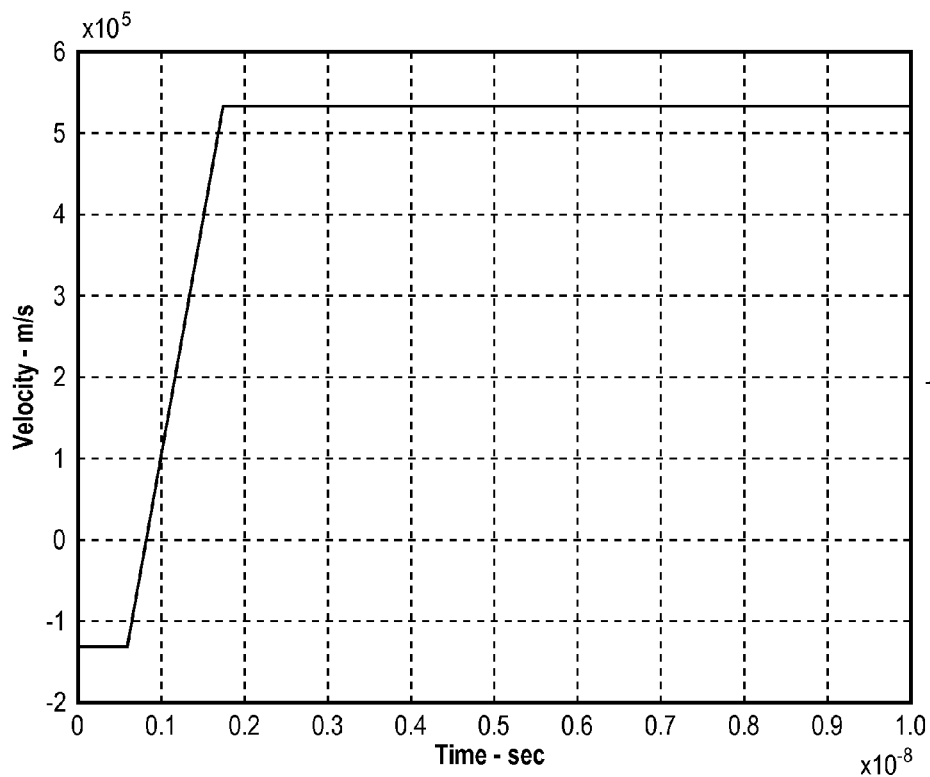
FIG. 16 is a graphical view of an input velocity of $-1.0 \times 10^6$ m/s
Figure 17:
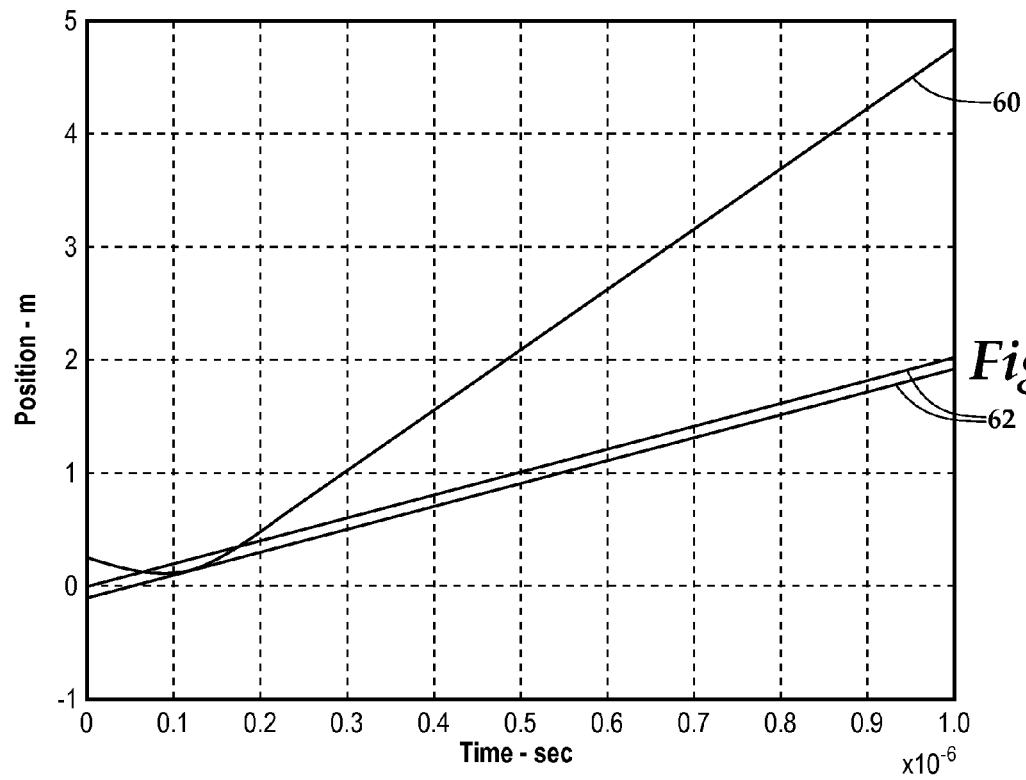
FIG. 17 is a graphical view of the velocity gain with the input velocity of FIG. 16.
Figure 18:
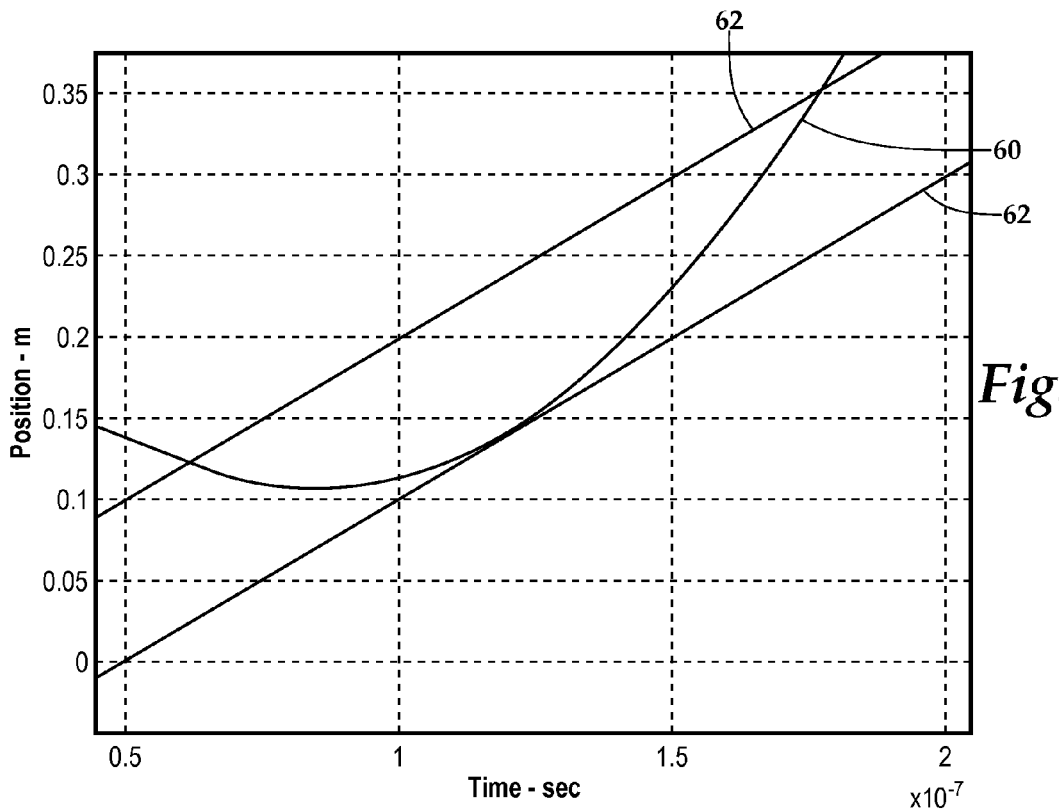
FIG. 18 is a graphical view of an enlarged portion of the graph of FIG. 17.

The computer programs for Mathlab ODE45: Ion particle Dynamics in an Accelerating Electric Field, and Electric Field Assist Ion Accelerator below are used to provide simulation curves which show varying the injection velocity of deuteron ions 60 with respect to the voltage wave 62 produced input pulse. 10 shows the input velocity of $1.3 \times 10^6$ m/s and for this input velocity FIG. 11 shows a velocity gain to $2.5 \times 10^6$ m/s. FIG. 12 shows the interaction of the injected ions with the voltage wave in the accelerator of the disclosed type. FIG. 13 shows the input velocity of 0 m/s and for this input velocity FIG. 14 shows a velocity gain to $4 \times 10^6$ m/s. FIG. 15 shows the interaction of the injected ions with the voltage wave in the accelerator of the disclosed type. FIG. 16 shows the input velocity of $-1.0 \times 10^6$ m/s this is possible in relation to the forward velocity of the moving field of the accelerator, i.e., the injection take place against the direction of the moving field. For this input velocity FIG. 17 shows a velocity gain to $4.8 \times 10^6$ m/s. FIG. 18 shows the interaction of the injected ions with the voltage wave in the accelerator of the disclosed type. Thus by injecting the ions into the accelerator in front of the voltage wave 62 with a negative velocity, a greater acceleration is produced on the ion 60 by the voltage wave 62.

Figure 7:
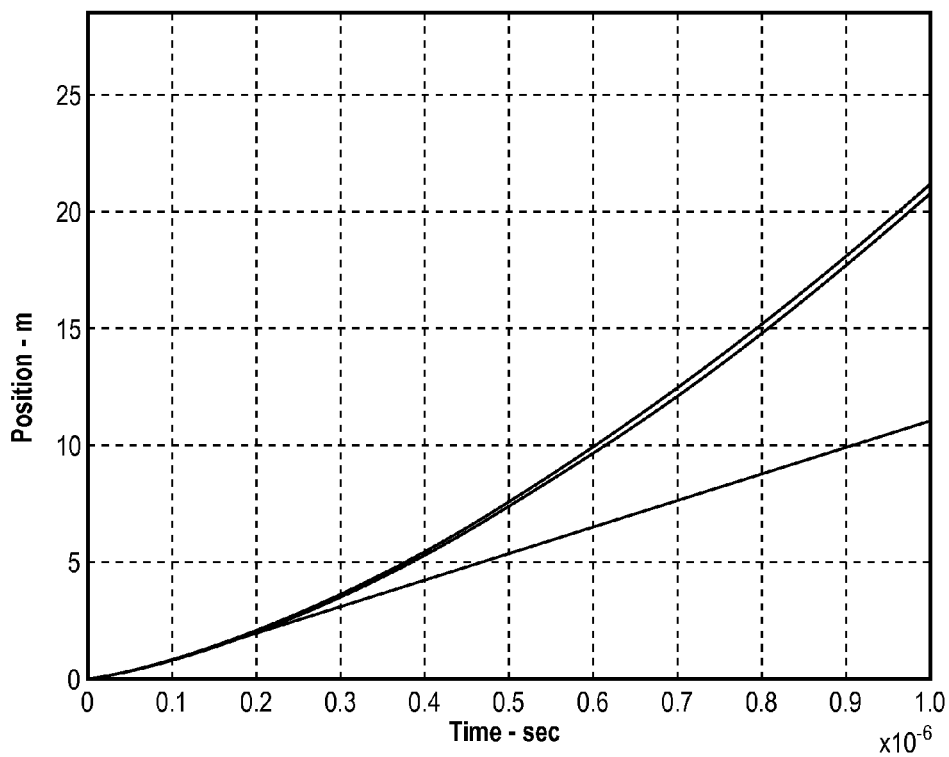
FIG. 7 is a graphical view of an accelerating voltage wave in vs. a constant velocity voltage wave.
Figure 10:
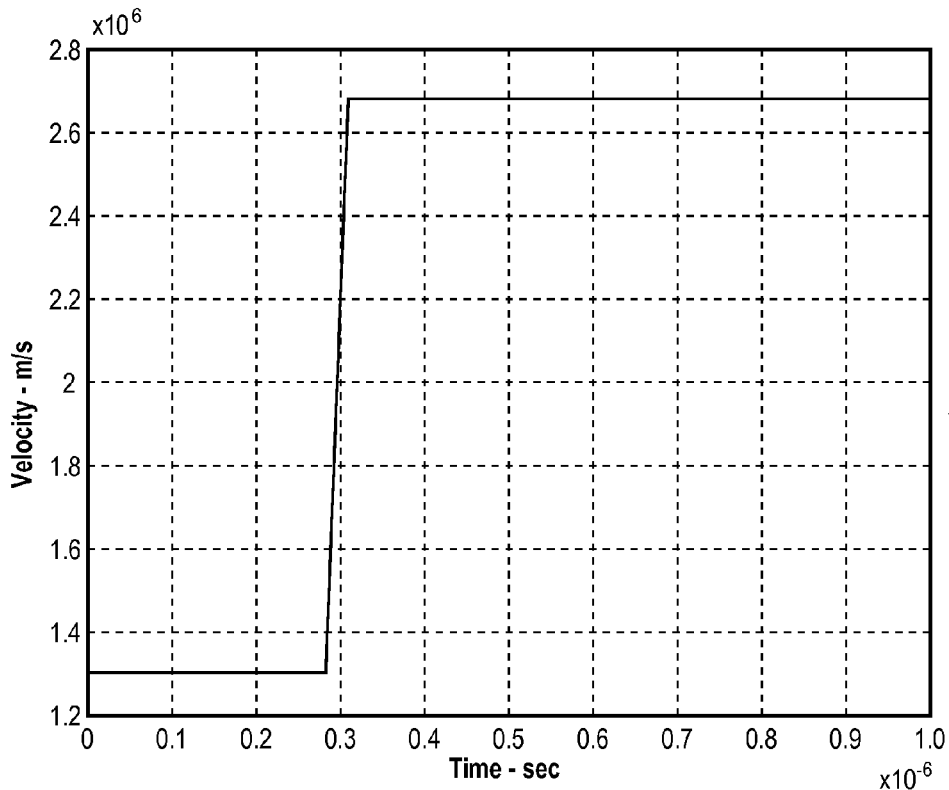
FIG. 10 is a graphical view of an input velocity of $1.3 \times 10^6$ m/s.
Figure 8:
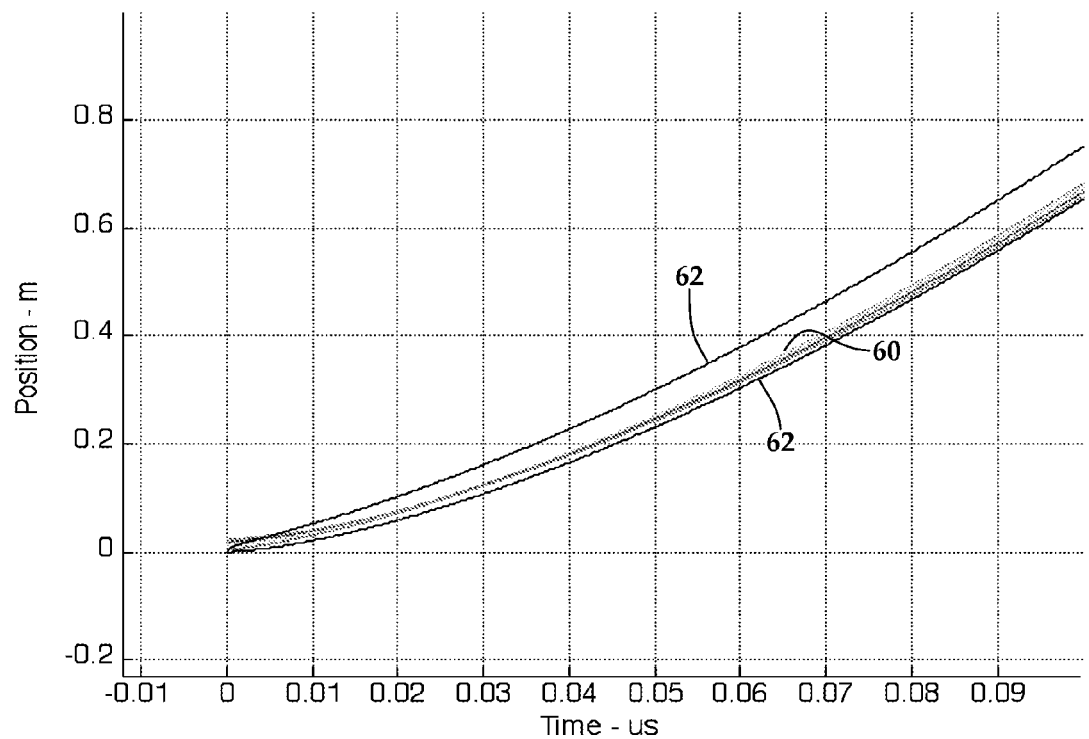
FIG. 8 is a graphical view of how a voltage wave compresses the velocity dispersion of injected deuterium ions.
Figure 9:
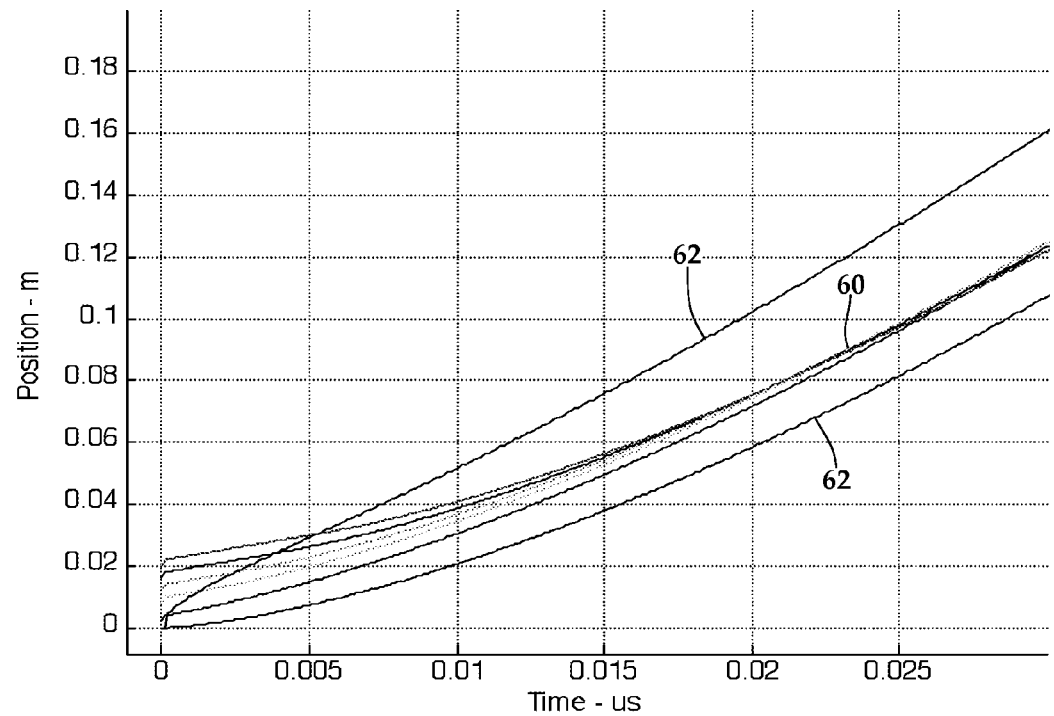
FIG. 9 is a graphical view of an enlarged portion of the graph of FIG. 8

The output of the program in FIG. 7 shows the acceleration of the voltage wave in (upper curve) vs. a constant velocity voltage wave (lower curve). FIG. 8 shows how the voltage wave compress the velocity dispersion of injected deuterium ions. FIG. 9 shows how the voltage wave compresses the velocity dispersion of injected deuterium ions up to about $0.03 \times 10^{-6}$ seconds and that dispersion of injected deuterium ions increases after $0.03 \times 10^{-6}$ seconds.

The deuteron ions are directed at a target 58 shown in FIG. 3 containing deuteron atoms, typically absorbed as $D_2$ in a thin layer of Titanium or palladium on a thermally conductive substrate such as copper or silver. It should be understood that deuterium gas, or deuterium hydrides, or deuterium containing liquids could be used.

Design Equations

The conservation of energy and the conservation of momentum are used to generate the controlling equations for particle dynamics. If nuclear fission or fusion is involved then Einstein's equation relating energy to mass must be included.

Two particles undergoing an elastic collision with initial velocities $u_1$ and $u_2$ and final velocities $v_1$ and $v_2$.

$$v_1 = (u_1(m_1 - m_2) + 2m_2 u_2)/(m_1 + m_2)$$

$$v_2 = (u_2(m_2 - m_1) + 2m_1 u_1)/(m_1 + m_2)$$

The velocities $u_1$ and $u_2$ are the initial velocities of mass $m_1$ and $m_2$ respectively. The velocities are the final velocities of mass $m_1$ and $m_2$ respectively. If the mass $m_2$ is allowed to go to zero in the limit the following equations are generated.

$$v_1 = u_1$$

$$v_2 = 2u_1 - u_2$$

The velocities are vectors but the equations are one dimensional and therefore the signs will determine their direction. The equations can be rewritten with variables that represent use in ion acceleration.

$v_p$—velocity of the ion particle
$v_{pw}$—velocity of the pulse wave
q—the unit charge
m—the mass of a ion
$V_p$— voltage to accelerate the ion
$V_i$— voltage used by the injector
$v_f$—final ion velocity To calculate the final velocity $v_f$ we derive the following equation.

$$v_f = 2v_{pw} - v_p$$

$$v_{pw} = \sqrt{2V_p q/m} + v_p$$

$$v_p = \sqrt{2V_i q/m}$$

$$v_f^2 = (2q/m) \times (2\sqrt{V_p} + \sqrt{V_i})^2$$

$$v_f = \sqrt{(2q/m) \times (2\sqrt{V_p} + \sqrt{V_i})^2}$$

The equations will be derived that describe how the velocity should change with the position along the accelerator and how the velocity versus position profile can be obtained by varying the geometry of the accelerator and/or the winding pitch.

The derivation is a one dimensional second order solution ignoring such things as space charge, beam loading, pulse injection and removal, beam current luminance, and focusing.

An accelerating ion in an electric field providing maximum acceleration can be calculated as follows.

$$f = ma \text{ and } f = qE$$

The unit of charge is q and the electric field is E.
The electric field can be calculated as the voltage V divided by the length of the field d $$E = V/d$$

The variable d is equal to $d = v \times t_r$ where v is the current velocity and $t_r$ is the electric field rise time.

Combing these equations with acceleration on the left hand side:

$$a = \frac{dv}{dt} = \frac{qV}{md} = qV/mt_r v$$

Using separation of variables:

$$v \times dv = qV/mt_r \times dt$$

Integrating both sides and rearranging terms we obtain:

$v^2 = 2qV/mt_r \times \text{time}$ $v = \sqrt{2qV/mt_r \times \text{time}}$

To find the equation for position we integrate velocity with respect to time.

$p = 2/3 \times \sqrt{2qV/mt_r \times \text{time}^3}$

Using the equations for velocity and position we can calculate velocity as a function of position. This result will be used to determine the geometry of the accelerator.

$v_2 = 2qV/mt_r \times \text{time}$

Solving for time $\text{time} = v^2 mt_r/qV$

This result can be used in place of time in the position equation and we can solve for velocity as a function of position along the accelerator.

$p = \frac{2}{3} \times \sqrt{\frac{2qV}{mt_r} \times (v^2 mt_r/2qV)^3}$ $p = \frac{2}{3} \times \sqrt{v^6 \times (mt_r/2qV)^2}$ $p = \frac{2}{3} \times v^3 \times \frac{mt_r}{2qV}$ $p = v^3 \times mt_r/3qV$ Finally we have:

$v = \sqrt[3]{3qV \times p/mt_r}$

For a transmission line:

$Z = \sqrt{L/C}$ $v = 1/\sqrt{LC}$

Therefore:

$\frac{1}{\sqrt{LC}} = \sqrt[3]{3qV \times p/mt_r}$

Squaring both sides and rearranging terms we have:

$$LC = \left(\frac{mt_r}{3qV \times p}\right)^{2/3}$$

The equations (Briggs 2006) that describe the inductance and capacitance per unit length of a coaxial cable with a helical wound center are:

$$L = \pi n^2 a^2 \mu_0 \left(1 - \frac{a^2}{b^2}\right)$$

$$C = \frac{2\pi\varepsilon}{\ln\left(\frac{b}{a}\right)}$$

Where the diameter of the helical coil is a, the diameter of the outer shield is b, the number of turns is n, the relative magnetic permeability is $\mu_0$, and the electric permittivity is $\in$. All units are per unit length.

Combining the last three equations provides multiple solutions by varying a, b and n. There are a number of simplifications that could be made such as allowing the ratio of a/b to be constant. The values of these three variables should have optimum values.

$$LC = \left(\frac{mt_r}{3qV \times p}\right)^{2/3}$$

$$LC = \pi n^2 a^2 \mu_0 \left(1 - \frac{a^2}{b^2}\right) \times \frac{2\pi\varepsilon}{\ln\left(\frac{b}{a}\right)}$$

Keeping the ratio constant and the number of turns per unit length constant we get the following equation:

$$a = k \times \frac{1}{\sqrt[3]{p}}$$

It should be understood that where a single accelerator section 22 having a hollow dielectric pipe, coil outer metal pipe and pulse generator is described multiple accelerator sections 22 could be used to increase the acceleration of ions as shown in FIG. 5a.

Figure 19:
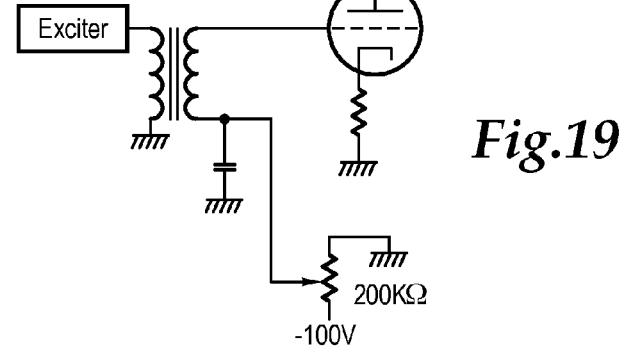
FIG. 19 is a schematic illustration of an alternative drive circuit forming the pulse generator of this invention based on a vacuum tube.

It should be understood that various pulse generators could be used, such as those shown in U.S. Pat. No. 2,465,840 to Alan Dower Blumlein Deceased, or an alternative drive circuit could form the pulse generator based on the vacuum tube as illustrated in FIG. 19.

It is understood that the invention is not limited to the particular construction and arrangement of parts herein illustrated and described, but embraces all such modified forms thereof as come within the scope of the following claims.

A portion of the disclosure of this patent document contains material which is subject to copyright protection. The copyright or mask work owner has no objection to the facsimile reproduction by anyone of the patent document or the patent disclosure, as it appears in the Patent and Trademark Office patent file or records, but otherwise reserves all copyright rights whatsoever.

```
%************************************************************
% Title: Ion Particle Dynamics in an Accelerating Electric Field
%
%************************************************************
% Particle is injected with a velocity of 1.58m/us (25kV) and just ahead of
% the electric field. Time is in us, velocity is in m/us, and position is
% is meters. Assume 100kV pulse with 10ns rise time.
%--------------------------------------------------------------
% initialize the system
%--------------------------------------------------------------
clc;
close all;
clear all;
%--------------------------------------------------------------
% declare and initialize the physical constants and parameters
%--------------------------------------------------------------
m = 3.3445e-27;         %mass of deuteron
q = 1.60218e-19;        %charge on deuteron
V = 200e3;              %voltage
tr = 0.02;              %rise time in us
dt = 1e-4;              %1ns
time = 0:dt:0.9999;     %0-1000ns
aconst = (q*V/(m*tr))*1e-12;
acc = zeros(5,10000);
vel = zeros(5,10000);
pos = zeros(5,10000);
Ef = zeros(1,10000);
Eb = zeros(1,10000);
%--------------------------------------------------------------
% analytical solution
%--------------------------------------------------------------
v = sqrt(2*aconst*time);
p = (2/3)*sqrt(2*aconst*time.^3);
%--------------------------------------------------------------
% MatLab ODE45 solution.
%--------------------------------------------------------------
[T Y] = ode45(@soln, [0 1], [1.58 0.004]);
A = aconst./Y(:,1);
%--------------------------------------------------------------
% numerical solution describing the motion of the deuterons
%--------------------------------------------------------------
pos(1,1) = 0.002; %red
pos(2,1) = 0.008; %cyan
pos(3,1) = 0.012; %green
pos(4,1) = 0.016; %blue
pos(5,1) = 0.020; %magenta
d = 0.002;
pos(1,2) = pos(1,1)+d; %red
pos(2,2) = pos(2,1)+d; %cyan
pos(3,2) = pos(3,1)+d; %green
pos(4,2) = pos(4,1)+d; %blue
pos(5,2) = pos(5,1)+d; %magenta
for j = 1:5
   acc(j,1) = 303.1957;
   vel(j,1) = 1.55;
   acc(j,2) = 300.3091;
   vel(j,2) = 1.57;
   for k = 3:10000
      Eb(k) = p(k);
      Ef(k) = p(k) + v(k)*tr;
      if (pos (j,k-1) >= Eb(k) && pos (j,k-1) <= Ef(k))
         acc (j,k) = aconst/((3*vel (j,k-2) - vel(j,k-1))/2) ;
      else
         acc(j,k) = 0;
      end
      vel(j,k) = vel (j,k-1) + (acc(j,k) + acc(j,k-1))*dt/2;
      pos(j,k) = pos(j,k-1) + (vel(j,k) + vel(j,k-1))*dt/2;
   end
end
%--------------------------------------------------------------
% plot the results
%--------------------------------------------------------------
figure(1);
grid on;
hold on;
plot(time,pos(1,:),'r');
plot(time,pos(2,:),'c');
plot(time,pos(3,:),'g'):
plot(time,pos(4,:),'b');
plot(time,pos(5,:),'m');
plot(time,Eb,'k');
plot(time,Ef,'k');
xlabel('Time - us')
ylabel('Position - m');
figure(2);
hold on;
grid on;
plot(time,vel(1,:),'r');
plot(time,vel(2,:),' c');
plot(time,vel(3,:),'g');
plot(time,vel(4,:),'b');
plot(time,vel(5,:),'m');
xlabel('Time - us');
ylabel('Velocity - m/us ');
figure(3);
hold on;
grid on;
plot(pos(1,:),vel(1,:),'r');
plot(pos(2,:),vel(2,:),'c');
plot(pos(3,:),vel(3,:),'g');
plot(pos(4,:),vel(4,:),'b');
plot(pos(5,:),vel(5,:),'m');
xlabel('Position - m');
ylabel('Velocity - m/us');
axis([0 10 0 25]);
figure(4);
hold on;
grid on;
plot(time,acc(1,:),'r');
plot(time,acc(2,:),'c');
plot(time,acc(3,:),'g');
plot(time,acc(4,:),'b');
plot(time,acc(5,:),'m');
xlabel('Time - us');
ylabel('Acceleration - m/us^2');
axis([0 1 0 300]);
%--------------------------------------------------------------
%print the results
%--------------------------------------------------------------
fprintf('Time\t\tPosition\tVelocity\r\n');
for j=1:length(T)
   fprintf('%f\t%f\t%f\r', T(j), Y(j,2), Y(j,1));
end
%--------------------------------------------------------------
% end of file
%--------------------------------------------------------------

%************************************************************
% Title: Electric Field Assist Ion Accelerator.m
%
%************************************************************
%
%
%
%************************************************************
% 800kV/m
% units - m, m/us, and m/us^2
% electric field is moving at 2m/us
%--------------------------------------------------------------
% initialze the system
%--------------------------------------------------------------
clc;
close all;
clear all;
%--------------------------------------------------------------
% declare and initialize the physical constants - SI Units
%--------------------------------------------------------------
tr = 0.1;               %rise time in us
Ev = 2.0;               %velocity of electric field - m/us
Ed = Ev*tr;             %length of electric field - m
```

-continued

```
m = 3.3445e-27;        %mass of deuteron
q = 1.60218e-19;       %charge on deuteron
V = 100e3;             %voltage
ac = q*V/(m*Ed)*1e-12; %acceleration
%----------------------------------------------------------------
% declare and initialize the parameters
%----------------------------------------------------------------
dt = 1e-3;             %1ns
time = 0:dt:0.499;     %0-1us
acc = zeros(5,500);
vel = zeros(5,500);
pos = zeros(5,500);
Eb = zeros(1,500);
Ef = zeros(1,500);
Eb(1:1) = 0.0;
Ef(1:2) = Ed;
vel(:,1:2) = -1;
pos(1,1:2) = Ed + 0.28;
pos(2,1:2) = Ed + 0.26;
pos(3,1:2) = Ed + 0.24;
pos(4,1:2) = Ed + 0.22;
pos(5,1:2) = Ed + 0.20;
%----------------------------------------------------------------
% run the simulation
%----------------------------------------------------------------
for p = 1:5
   for j = 3:500
      Eb(j) = Ev*time(j-1);
      Ef(j) = Eb(j-1) + Ed;
      if(pos(p,j-1) >= Eb(j) && pos(p,j-1) <= Ef(j-1))
         acc(p,j) = ac;
      else
         acc(p,j) = 0;
      end
      vel(p,j) = vel(p,j-1) + (3*acc(p,j) - acc(p,j-1))*dt/2;
      pos(p,j) = pos(p,j-1) + (vel(p,j) + vel(p,j-1))*dt/2;
   end
end
%----------------------------------------------------------------
% plot the results
%----------------------------------------------------------------
figure(1);
grid on;
hold on;
plot(time,Ef,'k');
plot(time,Eb,'k');
xlabel('Time - us');
ylabel('Position - m');
plot(time,pos(1,:),'r');
plot(time,pos(2,:),'c');
plot(time,pos(3,:),'g');
plot(time,pos(4,:),'b');
plot(time,pos(5,:),'m');
figure(2);
plot(time,vel(:,:));
hold on;
grid on;
xlabel('Time - us');
ylabel('Velocity - m/us');
%----------------------------------------------------------------
% end of file
%----------------------------------------------------------------
```

I claim:

1. A helical ion accelerator and neutron source comprising:
an ion source;
a dielectric conical pipe defining an outer conical surface, an inner vacuum chamber, and defining an axis of the dielectric conical pipe;
an outer conductive wire wound about the outer conical surface to form a coil of wire which is circumferentially wrapped around the outer conical surface and evenly spaced along the axis;
wherein the conductive wire forming a part of the coil defines a proximal end and a distal end, and wherein the outer conical surface tapers from the proximal end to the distal end;
wherein the vacuum chamber is connected to a source of vacuum;
an outer conical metal pipe which is coaxial with the axis of the dielectric conical pipe, the outer conical metal pipe defining an inner conical surface which is spaced from the outer conical surface of the dielectric conical pipe, and from the coil of wire wrapped around said outer conical surface;
a 100 to 300 kV pulse wave voltage source connected to the proximal end of the coil through a resistive column, an induction coil of at least one turn, or formed by charging the outer conical metal pipe, or wherein said 100 to 300 kV pulse wave voltage source is formed by the outer conical metal pipe connected by a high-voltage switch to the proximal end of the coil;
a solenoid magnet of at least 0.25 Tesla defining an inner cylindrical/conical solenoid cavity, said cavity symmetrically aligned along the axis so that the outer conical metal pipe with solenoid magnet surrounds the coil and the dielectric conical pipe; and
a target positioned along an extension of the axis, so as to produce a beam of neutrons through fusion.

2. The helical ion accelerator and neutron source of claim 1 wherein the dielectric conical pipe defines a' first radius with respect to the axis at every point along the axis, and wherein the outer conical metal pipe defines a second radius with respect to the axis at every point along the axis, and wherein the ratio of the first radius to the second radius at each point along the axis is a constant.

3. A neutron beam inspection device comprising:
a deuteron ion source;
a dielectric conical pipe defining an outer conical surface, an inner vacuum chamber, and defining an axis of the dielectric conical pipe;
an outer conductive wire wound about the outer conical surface to form a coil of wire which is circumferentially wrapped around the outer conical surface and evenly spaced along the axis;
wherein the conductive wire forming a part of the coil defines a proximal end and a distal end, and wherein the outer conical surface tapers from the proximal end to the distal end;
wherein the vacuum chamber is connected to a source of vacuum;
an outer conical metal pipe which is coaxial with the axis of the dielectric conical pipe, the outer conical metal pipe defining an inner conical surface which is spaced from the outer conical surface of the dielectric conical pipe, and from the coil of wire wrapped around said outer conical surface;
a 100 to 300 kV pulse wave voltage source connected to the proximal end of the coil through a resistive column, an induction of one to a few coils, or formed by charging the outer conical metal pipe wherein said outer conical metal pipe is connected by a high-voltage switch to the proximal end of the coil;
a solenoid magnet of at least 0.25 Tesla defining an inner cylindrical or conical solenoid cavity, said cavity symmetrically aligned along the axis so that the outer conical metal pipe is surrounded by the solenoid magnet;
a target comprising a quantity of deuterium positioned along an extension of the axis, so as to produce a beam of neutrons through the fusion of beam deuterons with deuterons in the target;
an inspection target; and
a neutron imaging camera.

4. A method of generating neutrons comprising the steps of:
- generating positive deuteron ions from an ion source;
- injecting the deuteron ions with an injection velocity of about 25 kV or 1.5 meters/microsecond along a central axis of a helical ion accelerator;
- accelerating the ionized deuterium along an axis of the helical ion accelerator by applying a voltage pulse of about 100 to 300 kV to a coil wrapped around a dielectric pipe, the coil surrounded by a dielectric fluid and enclosed in an outer conical metal pipe, while maintaining a vacuum within the dielectric pipe, so causing an electromagnetic wave to propagate along the axis of the dielectric pipe of the helical ion accelerator which is formed by the coil wrapped around the dielectric pipe;
- wherein the coil has a proximal end and a distal end and the voltage pulse is applied to the proximal end of the coil through a resistive column, by charging the outer conical metal pipe and shorting said outer pipe to the proximal end of the coil, or by applying a current through an inductor of one to a few coils, wrapped around the proximal end of said coil to induce said high voltage pulse in said coil;
- radially focusing the deuteron ions in the accelerator by the application of a solenoid magnetic field of 0.25 to 3 Tesla aligned along the axis of the accelerator;
- accelerating the electromagnetic wave as it propagates along the axis of the dielectric pipe of the helical ion accelerator by tapering the impedance of the accelerator in the direction of wave propagation to reduce the impedance per unit length of the accelerator;
- wherein the tapering of the impedance of the accelerator in the direction of wave propagation is accomplished by varying the geometry of the accelerator by tapering the coil and the outer conical metal pipe along the axis of acceleration.

5. The method of claim 4 wherein the injection velocity of the deuteron ions is at a velocity slower than the electromagnetic wave at injection so as to increase the velocity of the deuteron ions at the distal end of the coil.

6. The method of claim 4 wherein the tapering of the impedance of the accelerator in the direction of wave propagation is accomplished by varying the geometry of the accelerator by tapering the coil and the outer metal pipe along the axis of acceleration to maintain a constant ratio between a radius defined by the coil and a radius defined by the outer metal pipe.

7. The method of claim 4 wherein the tapering of the impedance of the accelerator in the direction of wave propagation is accomplished by decreasing the number of turns of the coil per meter along the axis of acceleration.

* * * * *